(12) United States Patent
Rudnic et al.

(10) Patent No.: US 7,157,095 B2
(45) Date of Patent: Jan. 2, 2007

(54) MULTIPLE-DELAYED RELEASE ANTIFUNGAL PRODUCT, USE AND FORMULATION THEREOF

(75) Inventors: Edward M. Rudnic, N. Potomac, MD (US); James D. Isbister, Potomac, MD (US); Donald J. Treacy, Jr., Annapolis, MD (US); Sandra E. Wassink, Frederick, MD (US)

(73) Assignee: Advancis Pharmaceutical Corporation, Germantown, MD (US)

( * ) Notice: Subject to any disclaimer, the term of this patent is extended or adjusted under 35 U.S.C. 154(b) by 0 days.

(21) Appl. No.: 10/211,682

(22) Filed: Aug. 2, 2002

(65) Prior Publication Data

US 2003/0147953 A1   Aug. 7, 2003

Related U.S. Application Data

(63) Continuation-in-part of application No. 09/792,189, filed on Feb. 22, 2001, now abandoned, which is a continuation-in-part of application No. 09/687,229, filed on Oct. 13, 2000, now abandoned.

(51) Int. Cl.
*A01N 25/34* (2006.01)
*A61K 9/58* (2006.01)

(52) U.S. Cl. ............... 424/408; 424/462; 424/469; 424/471; 424/472

(58) Field of Classification Search ............... 424/400, 424/489, 490, 451, 457, 458, 463
See application file for complete search history.

(56) References Cited

U.S. PATENT DOCUMENTS

| | | | |
|---|---|---|---|
| 4,435,173 A | 3/1984 | Siposs et al. | 609/155 |
| 4,616,008 A | 10/1986 | Hirai et al. | 514/200 |
| 4,794,001 A | 12/1988 | Mehta et al. | 424/458 |
| 4,831,025 A | 5/1989 | Godtfredsen et al. | 514/195 |
| 4,904,476 A | 2/1990 | Mehta et al. | 424/456 |
| 4,915,953 A | 4/1990 | Jordan et al. | 424/473 |
| 4,971,805 A | 11/1990 | Kitanishi et al. | 424/494 |
| 5,011,692 A | 4/1991 | Fujioka et al. | 424/426 |
| 5,110,597 A | 5/1992 | Wong et al. | 424/438 |
| 5,213,808 A | 5/1993 | Bar-Shalom et al. | 424/473 |
| 5,229,131 A | 7/1993 | Amidon et al. | 424/451 |
| 5,395,626 A | 3/1995 | Kotwal et al. | 424/472 |
| 5,401,512 A | 3/1995 | Rhodes et al. | 424/458 |
| 5,414,014 A | 5/1995 | Schneider et al. | 514/535 |
| 5,445,829 A | 8/1995 | Paradissis et al. | 424/480 |
| 5,462,747 A | 10/1995 | Radebaugh et al. | 424/465 |
| 5,472,708 A | 12/1995 | Chen | 424/451 |
| 5,508,040 A | 4/1996 | Chen | 424/451 |
| 5,567,441 A | 10/1996 | Chen | 424/494 |
| 5,672,359 A * | 9/1997 | Digenis et al. | 424/463 |
| 5,719,132 A | 2/1998 | Lin et al. | 514/50 |
| 5,827,531 A | 10/1998 | Morrison et al. | 424/450 |
| 5,840,329 A | 11/1998 | Bai | 424/458 |
| 5,877,243 A | 3/1999 | Sarangapani | 524/139 |
| 5,910,322 A | 6/1999 | Rivett et al. | 424/484 |
| 6,027,748 A | 2/2000 | Conte et al. | 424/458 |
| 6,132,771 A | 10/2000 | Depui et al. | 424/468 |
| 6,294,199 B1 | 9/2001 | Conley et al. | 424/468 |
| 6,333,050 B1 * | 12/2001 | Wong et al. | 424/473 |
| 6,358,525 B1 | 3/2002 | Guo et al. | 424/464 |
| 6,610,323 B1 * | 8/2003 | Lundberg et al. | 424/458 |
| 2001/0046984 A1 | 11/2001 | Rudnic et al. | 514/210.09 |
| 2001/0048944 A1 | 12/2001 | Rudnic et al. | 424/468 |
| 2002/0004070 A1 | 1/2002 | Rudnic et al. | 424/468 |
| 2002/0004499 A1 | 1/2002 | Rudnic et al. | 514/192 |

FOREIGN PATENT DOCUMENTS

| WO | WO 94/27557 | 12/1994 |
|---|---|---|
| WO | WO 95/20946 | 8/1995 |
| WO | WO 96/04908 | 2/1996 |
| WO | WO 98/22091 | 5/1998 |

\* cited by examiner

*Primary Examiner*—Neil S. Levy
(74) *Attorney, Agent, or Firm*—Elliot M. Olstein; Raymond E. Stauffer

(57) ABSTRACT

An anti-fungal product is comprised of at least three delayed release dosages forms, each of which has a different release profile, with the $C_{max}$ for the anti-fungal product being reached in less than about twelve hours after initial release of anti-fungal from the product.

42 Claims, No Drawings

MULTIPLE-DELAYED RELEASE ANTIFUNGAL PRODUCT, USE AND FORMULATION THEREOF

This application is a continuation-in-part of U.S. application Ser. No. 09/792,189, filed on Feb. 22, 2001, now abandoned which is a continuation-in-part of U.S. application Ser. No. 09/687,229, filed on Oct. 13, 2000 now abandoned.

This invention relates to an anti-fungal product, as well as the use and formulation thereof.

A wide variety of anti-fungals have been used, and will be used, in order to combat bacterial infection. In general, such anti-fungals can be administered by a repeated dosing of immediate release dosage forms, which results in poor compliance or as a controlled release formulation (slow release) at higher administered doses. The present invention is directed to providing for an improved anti-fungal product.

In accordance with one aspect of the present invention, there is provided an anti-fungal pharmaceutical product which is comprised of at least two, preferably at least three, anti-fungal dosage forms. Such dosage forms are formulated so that each of the dosage forms has a different release profile.

In a particularly preferred embodiment, there are at least two, preferably at least three dosage forms, each of which has a different release profile and the release profile of each of the dosage forms is such that the dosage forms each start release of the anti-fungal contained therein at different times after administration of the anti-fungal product.

Thus, in accordance with an aspect of the present invention, there is provided a single or unitary anti-fungal product that has contained therein at least two, preferably at least three anti-fungal dosage forms, each of which has a different release profile, whereby the anti-fungal contained in each of such dosage forms is released at different times.

In accordance with a further aspect of the invention, the anti-fungal product may be comprised of at least four different dosage forms, each of which starts to release the anti-fungal contained therein at different times after administration of the anti-fungal product.

The anti-fungal product generally does not include more than five dosage forms with different release times.

In accordance with a preferred embodiment, the anti-fungal product has an overall release profile such that when administered the maximum serum concentration of the total anti-fungal released from the product is reached in less than twelve hours, preferably in less than eleven hours in each case after initial release of the anti-fungal. In an embodiment, the maximum serum concentration of the total anti-fungal released from the anti-fungal product is achieved no earlier than four hours after initial release of the anti-fungal.

In accordance with one preferred embodiment of the invention, there are at least three dosage forms, each of which is a delayed release dosage form (which may be a pH sensitive or a non-pH sensitive delayed dosage form, depending on the type of anti-fungal product). More particularly, the anti-fungal release from the second of the at least three dosage forms achieves a $C_{max}$ (maximum serum concentration in the serum) at a time after the anti-fungal released from the first of the at least three dosage forms achieves a $C_{max}$ in the serum, and the anti-fungal released from the third dosage form achieves a $C_{max}$ in the serum after the $C_{max}$ of anti-fungal released from the second dosage form. As used herein first, second, third, etc., refers to the order in which anti-fungal is released from the dosage form.

In one embodiment, the second of the at least two dosage forms initiates release of the anti-fungal contained therein at least one hour after the first dosage form initiates release, with the initiation of the release therefrom generally occurring no more than six hours after initiation of release of anti-fungal from the first dosage form of the at least three dosage forms.

In general, the first dosage form produces a $C_{max}$ for the anti-fungal released therefrom within from about 0.5 to about 2 hours after initiation of release, with the second dosage form of the at least three dosage forms producing a $C_{max}$ for the anti-fungal released therefrom in no more than about four hours after initiation of release from the first dosage form. Thus, $C_{max}$ for the second dosage form is achieved after $C_{max}$ for the first dosage form and generally in no more than about 2 to about 3.5 hours after $C_{max}$ is achieved from the first dosage form. In general, the $C_{max}$ for such second dosage form is achieved no earlier than two hours after initiation of release from the first dosage form; however, it is possible within the scope of the invention to achieve $C_{max}$ in a shorter period of time.

As hereinabove indicated, the anti-fungal product may contain at least three or at least four or more different dosage forms. For example, if the anti-fungal product includes a third dosage form, the anti-fungal released therefrom reaches a $C_{max}$ at a time later than the $C_{max}$ is achieved for the anti-fungal released from each of the first and second dosage forms. In a preferred embodiment, release of anti-fungal from the third dosage form is started after initiation of release of anti-fungal from both the first dosage form and the second dosage form. In one embodiment, $C_{max}$ for anti-fungal release from the third dosage form is achieved within eight hours after initiation of release from the first dosage form.

In general, the first dosage form initiates release of anti-fungal at a time later than anti-fungal would be released from an immediate release dosage form. For example, the first dosage form would initiate release within 1 to four hours after administration of the product.

In another embodiment, the anti-fungal product contains at least four delayed release dosage forms, with each of the at least four dosage forms having different release profiles, whereby the anti-fungal release from each of the at least four different dosage forms achieves a $C_{max}$ at a different time.

As hereinabove indicated, in a preferred embodiment, irrespective of whether the anti-fungal contains at least two or at least three or at least four different delayed release dosage forms each with a different release profile, $C_{max}$ for all the anti-fungal released from the anti-fungal product is achieved in less than twelve hours after release is initiated from the first dosage form., and more generally is achieved in less than eleven hours.

In a preferred embodiment, the anti-fungal product is a once a day product, whereby after administration of the anti-fungal product, no further product is administered during the day; i.e., the preferred regimen is that the product is administered only once over a twenty-four hour period. Thus, in accordance with the present invention, there is a single administration of an anti-fungal product with the anti-fungal being released in a manner such that overall anti-fungal release is effected with different release profiles in a manner such that the overall $C_{max}$ for the anti-fungal product is reached in less than twelve hours after first release of anti-fungal. The term single administration means that the total anti-fungal administered over a twenty-four hour period is administered at the same time, which can be a single tablet or capsule or two or more thereof, provided that they are administered at essentially the same time.

Applicant has found that a single dosage anti-fungal product comprised of at least three anti-fungal dosage forms each having a different release profile is an improvement over a single dosage anti-fungal product comprised of an anti-fungal dosage form having a single release profile. Each of the dosage forms of anti-fungal in a pharmaceutically acceptable carrier may have one or more anti-fungals and each of the dosage forms may have the same anti-fungal or different anti-fungals.

It is to be understood that when it is disclosed herein that a dosage form initiates release after another dosage form, such terminology means that the dosage form is designed and is intended to produce such later initiated release. It is known in the art, however, notwithstanding such design and intent, some "leakage" of anti-fungal may occur. Such "leakage" is not "release" as used herein.

If at least four dosage forms are used, the fourth of the at least four dosage form may be a sustained release dosage form or a delayed release dosage form. If the fourth dosage form is a sustained release dosage form, even though $C_{max}$ of the fourth dosage form of the at least four dosage forms is reached after the $C_{max}$ of each of the other dosage forms is reached, anti-fungal release from such fourth dosage form may be initiated prior to or after release from the second or third dosage form.

The anti-fungal product of the present invention, as hereinabove described, may be formulated for administration by a variety of routes of administration. For example, the anti-fungal product may be formulated in a way that is suitable for topical administration; administration in the eye or the ear; rectal or vaginal administration; as nose drops; by inhalation; as an injectable; or for oral administration. In a preferred embodiment, the anti-fungal product is formulated in a manner such that it is suitable for oral administration.

For example, in formulating the anti-fungal product for topical administration, such as by application to the skin, the at least two different dosage forms, each of which contains an anti-fungal, may be formulated for topical administration by including such dosage forms in an oil-in-water emulsion, or a water-in-oil emulsion. In such a formulation, the immediate release dosage form is in the continuous phase, and the delayed release dosage form is in a discontinuous phase. The formulation may also be produced in a manner for delivery of three dosage forms as hereinabove described. For example, there may be provided an oil-in-water-in-oil emulsion, with oil being a continuous phase that contains the immediate release component, water dispersed in the oil containing a first delayed release dosage form, and oil dispersed in the water containing a third delayed release dosage form.

It is also within the scope of the invention to provide an anti-fungal product in the form of a patch, which includes anti-fungal dosage forms having different release profiles, as hereinabove described.

In addition, the anti-fungal product may be formulated for use in the eye or ear or nose, for example, as a liquid emulsion. For example, the dosage form may be coated with a hydrophobic polymer whereby a dosage form is in the oil phase of the emulsion, and a dosage form may be coated with hydrophilic polymer, whereby a dosage form is in the water phase of the emulsion.

Furthermore, the anti-fungal product with at least three different dosage forms with different release profiles may be formulated for rectal or vaginal administration, as known in the art. This may take the form of a cream or emulsion, or other dissolvable dosage form similar to those used for topical administration.

As a further embodiment, the anti-fungal product may be formulated for use in inhalation therapy by coating the particles and micronizing the particles for inhalation.

In a preferred embodiment, the anti-fungal product is formulated in a manner suitable for oral administration. Thus, for example, for oral administration, each of the dosage forms may be used as a pellet or a particle, with a pellet or particle then being formed into a unitary pharmaceutical product, for example, in a capsule, or embedded in a tablet, or suspended in a liquid for oral administration.

Alternatively, in formulating an oral delivery system, each of the dosage forms of the product may be formulated as a tablet, with each of the tablets being put into a capsule to produce a unitary anti-fungal product. Thus, for example, anti-fungal products may include a first dosage form in the form of a tablet that is an immediate release tablet, and may also include two or more additional tablets, each of which provides for a delayed release of the anti-fungal, as hereinabove described, whereby the $C_{max}$ of the anti-fungal released from each of the tablets is reached at different times, with the $C_{max}$ of the total anti-fungal released from the anti-fungal product being achieved in less than twelve hours after anti-fungal is first released.

The formulation of an anti-fungal product including at least three dosage forms with different release profiles for different routes of administration is deemed to be within the skill of the art from the teachings herein. As known in the art, with respect to delayed release, the time of release can be controlled by the concentration of anti-fungals in the coating and/or the thickness of the coating.

In formulating an anti-fungal product in accordance with the invention, in one embodiment, the first dosage form of the product generally provides from about 20% to about 50% of the total dosage of anti-fungal to be delivered by the product, with such first dosage form generally providing at least 25% of the total dosage of the anti-fungal to be delivered by the product. In many cases, the first dosage form provides from about 20% to about 30% of the total dosage of anti-fungal to be delivered by the product; however, in some cases it may be desirable to have the first dosage form provide for about 45% to about 50% of the total dosage of anti-fungal to be delivered by the product.

The remaining dosage forms deliver the remainder of the anti-fungal. In one embodiment, each of the delayed release dosage forms after the first delayed release dosage form may provide about equal amounts of anti-fungal; however, they may also be formulated so as to provide different amounts.

In accordance with the present invention, each of the dosage forms contains the same anti-fungal; however, each of the dosage forms may contain more than one anti-fungal.

In one embodiment, where the composition contains three delayed release components, the first component provides from 20% to 35% (preferably 20% to 30%), by weight, of the total anti-fungal; where there is four delayed release components, the first delayed release component provides from 15% to 30%, by weight, of the total anti-fungal; and where there are five delayed release components, the first delayed release component provides from 10% to 25%, by weight, of the total anti-fungal.

With respect to the delayed release components, where there are three delayed release components, the second delayed release component provides from 30% to 60%, by weight, of the total anti-fungal provided by the second and third delayed release components with the third delayed release component providing the remainder of the anti-fungal.

Where there are four delayed release components, the second released component provides 20% to 35% by weight of the total anti-fungal provided by the second, third and fourth delayed release components, the next in time delayed release component provides from 20% to 40%, by weight, of the anti-fungal provided by the second, third and fourth delayed release components and the last in time providing the remainder of the anti-fungal provided by the second, third and fourth delayed release components.

When there are five delayed release components, the second delayed release component provides from 15% to 30%, by weight, the next in time delayed release component provides from 15% to 30%, the next in time delayed release component provides from 20% to 35%, by weight, and the last in time delayed release component provides from 20% to 35%, by weight, in each case of the total anti-fungal provided by the second, third, fourth and fifth delayed release components.

An Immediate Release Component

The immediate release portion of this system can be a mixture of ingredients that breaks down quickly after administration to release the anti-fungal. This can take the form of either a discrete pellet or granule that is mixed in with, or compressed with, the other three components.

The materials to be added to the anti-fungals for the immediate release component can be, but are not limited to, microcrystalline cellulose, corn starch, pregelatinized starch, potato starch, rice starch, sodium carboxymethyl starch, hydroxypropylcellulose, hydroxypropylmethylcellulose, hydroxyethylcellulose, ethylcellulose, chitosan, hydroxychitosan, hydroxymethylatedchitosan, cross-linked chitosan, cross-linked hydroxymethyl chitosan, maltodextrin, mannitol, sorbitol, dextrose, maltose, fructose, glucose, levulose, sucrose, polyvinylpyrrolidone (PVP), acrylic acid derivatives (Carbopol, Eudragit, etc.), polyethylene glycols, such a low molecular weight PEGs (PEG2000–10000) and high molecular weight PEGs (Polyox) with molecular weights above 20,000 daltons.

It may be useful to have these materials present in the range of 1.0 to 60% (W/W).

In addition, it may be useful to have other ingredients in this system to aid in the dissolution of the drug, or the breakdown of the component after ingestion or administration. These ingredients can be surfactants, such as sodium lauryl sulfate, sodium monoglycerate, sorbitan monooleate, sorbitan monooleate, polyoxyethylene sorbitan monooleate, glyceryl monostearate, glyceryl monooleate, glyceryl monobutyrate, one of the non-ionic surfactants such as the Pluronic line of surfactants, or any other material with surface active properties, or any combination of the above.

These materials may be present in the rate of 0.05–15% (W/W).

The Non-pH Sensitive Delayed Release Component

The components in this composition are the same immediate release unit, but with additional polymers integrated into the composition, or as coatings over the pellet or granule.

Materials that can be used to obtain a delay in release suitable for this component of the invention can be, but are not limited to, polyethylene glycol (PEG) with molecular weight above 4,000 daltons (Carbowax, Polyox), waxes such as white wax or bees wax, paraffin, acrylic acid derivatives (Eudragit), propylene glycol, and ethylcellulose.

Typically these materials can be present in the range of 0.5–25% (W/W) of this component.

The pH Sensitive (Enteric) Release Component

The components in this composition are the same as the immediate release component, but with additional polymers integrated into the composition, or as coatings over the pellet or granule.

The kind of materials useful for this purpose can be, but are not limited to, cellulose acetate pthalate, Eudragit L, and other pthalate salts of cellulose derivatives.

These materials can be present in concentrations from 4–20% (W/W).

Sustained Release Component

The components in this composition are the same as the immediate release component, but with additional polymers integrated into the composition, or as coatings over the pellet or granule.

The kind of materials useful for this purpose can be, but are not limited to, ethylcellulose,hydroxypropylmethylcellulose,hydroxypropylcellulose, hydroxyethylcellulose, carboxymethylcellulose, methylcellulose, nitrocellulose, Eudragit R, and Eudragit RL, Carbopol, or polyethylene glycols with molecular weights in excess of 8,000 daltons.

These materials can be present in concentrations from 4–20% (W/W).

As hereinabove indicated, the units comprising the anti-fungal composition of the present invention can be in the form of discrete pellets or particles contained in the capsule, or particles embedded in a tablet or suspended in a liquid suspension.

The anti-fungal composition of the present invention may be administered, for example, by any of the following routes of administration: sublingual, transmucosal, transdermal, parenteral, etc., and preferably is administered orally. The composition includes a therapeutically effective amount of the anti-fungal, which amount will vary with the anti-fungal to be used, the disease or infection to be treated, and the number of times that the composition is to be delivered in a day. The composition is administered to a host in an amount effective for treating a bacterial infection.

The following are representative examples of some anti-fungals that can be employed in the composition of the invention: amphotericin B, flucytosine, fluconazole, griseofulvin, miconazole nitrate, terbinafine hydrochloride, ketoconazole, itraconazole, undecylenic acid and chloroxylenol, ciclopirox, clotrimazole, butenafine hydrochloride, nystatin, naftifine hydrochloride, oxiconazole nitrate, selenium sulfide, econazole nitrate, terconazole, butoconazole nitrate, carbol-fuchsin, clioquinol, methylrosaniline chloride, sodium thiosulfate, sulconazole nitrate, terbinafine hydrochloride, tioconazole, tolnaftate, undecylenic acid and undecylenate salts (calcium undecylenate, copper undecylenate, zinc undecylenate)

The invention will be further described with respect to the following examples; however, the scope of the invention is not limited thereby. All percentages in this specification, unless otherwise specified, are by weight.

Non-pH Sensitive Delayed Release Component

Formulate the composition by mixing the ingredients in a suitable pharmaceutical mixer or granulator such as a planetary mixer, high-shear granulator, fluid bed granulator, or extruder, in the presence of water or other solvent, or in a hot melt process. If water or other solvent was used, dry the blend in a suitable pharmaceutical drier, such as a vacuum over or forced-air oven. Allow the product to cool, the product may be sieved or granulated, and compressed using a suitable tablet press, such as a rotary tablet press.

|  | Ingredient | Conc. (% W/W) |
|---|---|---|
| Example 1: | Fluorouracil | 65% (W/W) |
|  | Microcrystalline cellulose | 20 |
|  | Polyox | 7.5 |
|  | Croscarmellose sodium | 7.5 |
| Example 2: | Fluorouracil | 55% (W/W) |
|  | Microcrystalline cellulose | 25 |
|  | Polyox | 10 |
|  | Glyceryl monooleate | 10 |
| Example 3: | Fluorouracil | 75% (W/W) |
|  | Polyox | 10 |
|  | Hydroxypropylcellulose | 5 |
|  | Croscarmellose sodium | 10 |
| Example 4: | Dexamethasone | 65% (W/W) |
|  | Microcrystalline cellulose | 20 |
|  | Polyox | 7.5 |
|  | Croscarmellose sodium | 7.5 |
| Example 5: | Dexamethasone | 55% (W/W) |
|  | Microcrystalline cellulose | 25 |
|  | Polyox | 10 |
|  | Glyceryl monooleate | 10 |
| Example 6: | Dexamethasone | 75% (W/W) |
|  | Polyox | 10 |
|  | Hydroxypropylcellulose | 5 |
|  | Croscarmellose sodium | 10 |
| Example 7: | Valrubicin | 65% (W/W) |
|  | Microcrystalline cellulose | 20 |
|  | Polyox | 7.5 |
|  | Croscarmellose sodium | 7.5 |
| Example 8: | Valrubicin | 55% (W/W) |
|  | Microcrystalline cellulose | 25 |
|  | Polyox | 10 |
|  | Glyceryl monooleate | 10 |
| Example 9: | Valrubicin | 75% (W/W) |
|  | Polyox | 10 |
|  | Hydroxypropylcellulose | 5 |
|  | Croscarmellose sodium | 10 |
| Example 10: | Tretinoin | 65% (W/W) |
|  | Microcrystalline cellulose | 20 |
|  | Polyox | 7.5 |
|  | Croscarmellose sodium | 7.5 |
| Example 11: | Tretinoin | 55% (W/W) |
|  | Microcrystalline cellulose | 25 |
|  | Polyox | 10 |
|  | Glyceryl monooleate | 10 |
| Example 12: | Tretinoin | 75% (W/W) |
|  | Polyox | 10 |
|  | Hydroxypropylcellulose | 5 |
|  | Croscarmellose sodium | 10 |

Enteric Release Component

Formulate the ingredients by mixing the ingredients in a suitable pharmaceutical mixer or granulator such as a planetary mixer, high-shear granulator, fluid bed granulator, or extruder, in the presence of water or other solvent, or in a hot melt process. If water or other solvent was used, dry the blend in a suitable pharmaceutical drier, such as a vacuum oven or forced-air oven. Allow the product to cool, the product may be sieved or granulated, and compressed using a suitable tablet press, such as a rotary tablet press.

|  | Ingredient | Conc. (% W/W) |
|---|---|---|
| Example 13: | Fluconazole | 65% (W/W) |
|  | Microcrystalline cellulose | 20 |
|  | Cellulose Acetate Pthalate | 15 |
| Example 14: | Fluconazole | 55% (W/W) |
|  | Microcrystalline cellulose | 25 |
|  | Cellulose Acetate Pthalate | 10 |
|  | Hydroxypropylmethylcellulose | 10 |
| Example 15: | Fluconazole | 65% (W/W) |
|  | Polyox | 20 |
|  | Hydroxypropylcellulose pthalate | 10 |
|  | Eudragit L 30D | 5 |
| Example 16: | Fluconazole | 40% (W/W) |
|  | Microcrystalline Cellulose | 40 |
|  | Cellulose Acetate Pthalate | 10 |
| Example 17: | Ketoconazole | 70% (W/W) |
|  | Hydroxypropylcellulose pthalate | 15 |
|  | Croscarmellose sodium | 10 |
| Example 18: | Ketoconazole | 75% (W/W) |
|  | Polyethylene glycol 2000 | 10 |
|  | Eudragit L 30D | 15 |
| Example 19: | Ketoconazole | 40% (W/W) |
|  | Lactose | 50 |
|  | Eudgragit L 30D | 10 |
| Example 20: | Griseofulvin | 65% (W/W) |
|  | Microcrystalline Cellulose | 20 |
|  | Eudragit L 30D | 10 |
| Example 21: | Griseofulvin | 75% (W/W) |
|  | Microcrystalline Cellulose | 15 |
|  | Hydroxypropylcellulose pthalate | 10 |
| Example 22: | Griseofulvin | 80% (W/W) |
|  | Lactose | 10 |
|  | Eudragit L 30D | 10 |
| Example 23: | Griseofulvin | 70% (W/W) |
|  | Polyethylene glycol 4000 | 20 |
|  | Cellulose acetate pthalate | 10 |
| Example 24: | Terbinafine HCl | 60% (W/W) |
|  | Polyethylene glycol 2000 | 10 |
|  | Lactose | 20 |
|  | Eudragit L 30D | 10 |
| Example 25: | Terbinafine HCl | 70% (W/W) |
|  | Microcrystalline cellulose | 20 |
|  | Cellulose acetate pthalate | 10 |

Sustained Release Component

Formulate the composition by mixing the ingredients in a suitable pharmaceutical mixer or granulator such as a planetary mixer, high-shear granulator, fluid bed granulator, or extruder, in the presence of water or other solvent, or in a hot melt process. If water or other solvent was used, dry the blend in a suitable pharmaceutical drier, such as a vacuum oven or forced-air oven. Allow the product to cool, the product may be sieved or granulated, and compressed using a suitable tablet press, such as a rotary tablet press.

|  | Ingredient | Conc. (% W/W) |
|---|---|---|
| Example 26: | Fluconazole | 65% (W/W) |
|  | Ethylcellulose | 20 |
|  | Polyox | 10 |
|  | Hydroxypropylmethylcellulose | 5 |
| Example 27: | Fluconazole | 55% (W/W) |
|  | Lactose | 25 |
|  | Polyox | 10 |
|  | Glyceryl monooleate | 10 |
| Example 28: | Fluconazole | 70% (W/W) |
|  | Polyox | 20 |
|  | Hydroxypropylcellulose | 10 |
| Example 29: | Ketoconazole | 75% (W/W) |
|  | Lactose | 15 |
|  | Hydroxypropylcellulose | 5 |
|  | Ethylcellulose | 5 |
| Example 30: | Ketoconazole | 75% (W/W) |
|  | Polyethylene glycol 4000 | 10 |
|  | Lactose | 10 |
|  | Eudragit RL 30D | 5 |
| Example 31: | Ketoconazole | 80% (W/W) |
|  | Polyethylene glycol 8000 | 10 |
|  | Hydroxypropylmethylcellulose | 5 |
|  | Eudgragit RS 30D | 5 |

-continued

| | Ingredient | Conc. (% W/W) |
|---|---|---|
| Example 32: | Griseofulvin | 75% (W/W) |
| | Hydroxyethylcellulose | 10 |
| | Polyethylene glycol 4000 | 10 |
| | Hydroxypropylcellulose | 5 |
| Example 33: | Griseofulvin | 75% (W/W) |
| | Lactose | 10 |
| | Povidone (PVP) | 10 |
| | Polyethylene glycol 2000 | 5 |
| Example 34: | Terbinafine HCl | 75% (W/W) |
| | Polyethylene glycol 4000 | 10 |
| | Povidone (PVP) | 10 |
| | Hydroxypropylcellulose | 5 |
| Example 35: | Terbinafine HCl | 75% (W/W) |
| | Lactose | 15 |
| | Polyethylene glycol 4000 | 5 |
| | Polyvinylpyrrolidone | 5 |
| Example 36: | Ketoconazole | 40% (W/W) |
| | Eudragit S100 | 50 |
| | Triethyl Citrate | 10 |
| Example 37: | Ketoconazole | 50% (W/W) |
| | Sureteric | 50 |
| Example 38: | Ketoconazole | 50% (W/W) |
| | Eudragit S100 | 45 |
| | Triethyl Citrate | 5 |

All Delayed Release Three Pulses

EXAMPLE 39

Anti-fungal Pellet Formulation and Preparation Procedure

Pellet Formulations

The composition of the Anti-fungal pellets provided in Table 1.

TABLE 1

Composition of Anti-fungal Pellets

| Component | Percentage (%) |
|---|---|
| Anti-fungal drug | 92 |
| Avicel PH 101 | 6.0 |
| Polyoxyl 35 Castor Oil* | 1.0 |
| Hydroxypropyl methylcellulose, NF* | 1.0 |
| Purified Water | ** |
| Total | 100 |

*Hydroxypropyl methylcellulose and Cremaphor EL were added as a 2.9% w/w aqueous solution during wet massing.
**Removed during processing Preparation Procedure for Anti-fungal Pellets
  Blend Anti-fungal and Avicel® PH 101 using a high shear mixer.
  Add the hydroxypropyl methylcellulose and Polyoxyl 35 Castor Oil binder solution slowly into the powder blend under continuous mixing.
  Extrude the wet mass using an LCI Bench Top Granulator. The diameter of the screen of the Bench Top Granulator is 0.8 mm.
  Spheronize the extrudate using a QJ-230 Spheronizer using a small cross section plate.
  Dry the spheronized pellets at 60° C. using a fluid bed dryer until the exhaust temperature reaches 40° C.
  Pellets between 20 and 40 Mesh were collected for further processing.

Anti-fungal Pulse One Pellet Formulation and Preparation Procedure

Preparation of an AQOAT AS-LF Aqueous Coating Dispersion

Dispersion Formulation

The composition of the aqueous AQOAT AS-LF aqueous coating dispersion applied to the Anti-fungal pellets is provided below in Table 2.

TABLE 2

AQOAT AS-LF Aqueous Coating Dispersion

| Component | Percentage (%) |
|---|---|
| AQOAT AS-LF | 7.0 |
| Triethyl Citrate | 2.0 |
| Talc | 2.1 |
| Sodium lauryl sulfate | 0.2 |
| Purified Water* | 88.7 |
| Solid Content | 11.3 |
| Polymer Content | 7.0 |

*Removed during processing

Preparation Procedure for an AQOAT AS-LF Aqueous Dispersion
  Add triethyl citrate (TEC) to the purified water with stirring.
  Add the sodium lauryl sulfate (SLS) to the TEC dispersion with stirring and completely until completely dissolved.
  Add the AQOAT to the TEC/SLS dispersion and stir for at least 30 minutes.
  Add the talc to the AQOAT dispersion and until completely mixed and for at least 30 minutes.
  Screen the dispersion through a No. 60 mesh sieve prior to coating.
  Continue to stir the dispersion until the coating process is complete.

Coating Conditions for the Application of AQOAT AS-LF Aqueous Coating Dispersion The following coating parameters were used for coating of the AQOAT AS-LF film coating dispersion.

| | |
|---|---|
| Coating Equipment | STREA 1 ™ Table Top Laboratory Fluid Bed Coater |
| Spray nozzle diameter | 1.0 mm |
| Material Charge | 300 gram |
| Inlet Air Temperature | 48° C. |
| Outlet Air Temperature | 27° C. |
| Atomization Air Pressure | 1.6 Bar |
| Pump Rate | 3–4 gram per minute |

Coat Anti-fungal pellets with AQOAT AS-LF film coating dispersion such that you apply 30% coat weight gain to the pellets.

Anti-fungal Pulse Two Pellet Formulation and Preparation Procedure

Preparation of an AQOAT AS-HF Aqueous Coating Dispersion

Dispersion Formulation

The composition of the aqueous AQOAT AS-HF aqueous coating dispersion applied to the Anti-fungal pellets is provided below in Table 3.

TABLE 3

AQOAT AS-HF Aqueous Coating Dispersion

| Component | Percentage (%) |
|---|---|
| AQOAT AS-HF | 7.0 |
| Triethyl Citrate | 2.0 |
| Talc | 2.1 |
| Sodium lauryl sulfate | 0.2 |
| Purified Water* | 88.7 |
| Solid Content | 11.3 |
| Polymer Content | 7.0 |

*Removed during processing

Preparation Procedure for an AQOAT AS-HF Aqueous Dispersion

Add triethyl citrate (TEC) to the purified water with stirring.

Add the sodium lauryl sulfate (SLS) to the TEC dispersion with stirring and completely until completely dissolved.

Add the AQOAT to the TEC/SLS dispersion and stir for at least 30 minutes.

Add the talc to the AQOAT dispersion and until completely mixed and for at least 30 minutes.

Screen the dispersion through a No. 60 mesh sieve prior to coating.

Continue to stir the dispersion until the coating process is complete.

Coating Conditions for the Application of AQOAT AS-HF Aqueous Coating Dispersion The following coating parameters were used for coating of the AQOAT AS-HF film coating dispersion.

| Coating Equipment | STREA 1 ™ Table Top Laboratory Fluid Bed Coater |
|---|---|
| Spray nozzle diameter | 1.0 mm |
| Material Charge | 300 gram |
| Inlet Air Temperature | 48° C. |
| Outlet Air Temperature | 27° C. |
| Atomization Air Pressure | 1.6 Bar |
| Pump Rate | 3–4 gram per minute |

Coat Anti-fungal pellets with AQOAT AS-HF film coating dispersion such that you apply 30% coat weight gain to the pellets.

Anti-fungal Pulse Three Pellet Formulation and Preparation Procedure

Preparation of an Eudragit® FS 30D Aqueous Coating Dispersion

Dispersion Formulation

The composition of the aqueous Eudragit® FS 30D dispersion applied to the Anti-fungal pellets is provided below in Table 4.

TABLE 4

Eudragit® FS 30D Aqueous Coating Dispersion

| Component | Percentage (%) |
|---|---|
| Eudragit® FS 30D | 54.8 |
| Triethyl Citrate | 0.9 |
| Talc | 3.3 |
| Purified Water* | 41.0 |
| Solid Content | 20.6 |
| Polymer Content | 16.4 |

*Removed during processing

Preparation Procedure for an Eudragit® FS 30D Aqueous Dispersion

Disperse triethyl citrate (TEC) in the purified water.

Add the talc in the triethyl citrate dispersion.

Homogenize the dispersion using a homogenizer.

Add slowly the Eudragit® FS 30D dispersion to the talc/TEC dispersion with stirring.

Continue to stir the coating dispersion until the coating process is complete.

Coating Conditions for the Application of Eudragit FS30D Aqueous Coating Dispersion The following coating parameters were used for coating with each of the Eudragit® FS 30 D aqueous film coating.

| Coating Equipment | STREA 1 ™ Table Top Laboratory Fluid Bed Coater |
|---|---|
| Spray nozzle diameter | 1.2 mm |
| Material Charge | 300 gram |
| Inlet Air Temperature | 38° C. |
| Outlet Air Temperature | 22° C. |
| Atomization Air Pressure | 1.6 Bar |
| Pump Rate | 6 gram per minute |

Coat pellets with Eudragit FS 30D coating dispersion dispersion such that you apply 30% coat weight gain to the pellets.

Anti-fungal Tablets

Tableting of the Anti-fungal Pellets

TABLE 5

Composition of Anti-fungal Tablets

| Component | Percentage (%) |
|---|---|
| Silicified microcrystalline cellulose | 21.6 |
| Lactose monohydrate | 13.0 |
| Povidone | 5.0 |
| Pulse One Pellets | 18.3 |
| Pulse Two Pellets | 18.3 |
| Pulse Three Pellets | 18.3 |
| Croscarmellose sodium | 5.0 |
| Magnesium stearate | 0.5 |
| Total | 100 |

Blend the silicified microcrystalline cellulose, lactose monohydrate, povidone, colloidal silicon dioxide and Anti-fungal coated pellets for 15 minutes in a tumble blender.

Add the magnesium stearate to the blender, and blend for 5 minutes.

Compress the blend on a rotary tablet press.

The fill weight should be adjusted to achieve the desired dose.

Encapsulation of the Anti-fungal Pellets

Pellets are filled into hard gelatin capsules at a of 33.4%: 33.3%:33.3%:Pulse One, Pulse Two, and Pulse Three Pellets respectively. The capsule is filled with the three different pellets to achieve the desired dose.

The present invention is particularly advantageous in that there is provided an anti-fungal product which provides an improvement over twice a day administration of the anti-fungal and an improvement over a once a day administration of the anti-fungal.

Numerous modification and variations of the present invention are possible in light of the above teachings and therefore, within the scope of the appended claims the invention may be practiced otherwise than as particularly described.

All Delayed Release Four Pulses

EXAMPLE 40

Anti-fungal Pellet Formulation and Preparation Procedure

Pellet Formulations

The composition of the Anti-fungal pellets provided in Table 6.

TABLE 6

Composition of Anti-fungal Pellets

| Component | Percentage (%) |
|---|---|
| Anti-fungal drug | 92 |
| Avicel PH 101 | 6.0 |
| Polyoxyl 35 Castor Oil* | 1.0 |
| Hydroxypropyl methylcellulose, NF* | 1.0 |
| Purified Water | ** |
| Total | 100 |

*Hydroxypropyl methylcellulose and Cremaphor EL were added as a 2.9% w/w aqueous solution during wet massing.
**Removed during processing Preparation Procedure for Anti-fungal Pellets Blend Anti-fungal and Avicel® PH 101 using a high shear mixer.

Add the hydroxypropyl methylcellulose and Polyoxyl 35 Castor Oil binder solution slowly into the powder blend under continuous mixing.

Extrude the wet mass using an LCI Bench Top Granulator. The diameter of the screen of the Bench Top Granulator is 0.8 mm.

Spheronize the extrudate using a QJ-230 Spheronizer using a small cross section plate.

Dry the spheronized pellets at 60° C. using a fluid bed dryer until the exhaust temperature reaches 40° C.

Pellets between 20 and 40 Mesh were collected for further processing.

Anti-fungal Pulse One Pellet Formulation and Preparation Procedure

Preparation of an AQOAT AS-LF Aqueous Coating Dispersion

Dispersion Formulation

The composition of the aqueous AQOAT AS-LF aqueous coating dispersion applied to the Anti-fungal pellets is provided below in Table 7.

TABLE 7

AQOAT AS-LF Aqueous Coating Dispersion

| Component | Percentage (%) |
|---|---|
| AQOAT AS-LF | 7.0 |
| Triethyl Citrate | 2.0 |
| Talc | 2.1 |
| Sodium lauryl sulfate | 0.2 |
| Purified Water* | 88.7 |
| Solid Content | 11.3 |
| Polymer Content | 7.0 |

*Removed during processing

Preparation Procedure for an AQOAT AS-LF Aqueous Dispersion

Add triethyl citrate (TEC) to the purified water with stirring.

Add the sodium lauryl sulfate (SLS) to the TEC dispersion with stirring and completely until completely dissolved.

Add the AQOAT to the TEC/SLS dispersion and stir for at least 30 minutes.

Add the talc to the AQOAT dispersion and until completely mixed and for at least 30 minutes.

Screen the dispersion through a No. 60 mesh sieve prior to coating.

Continue to stir the dispersion until the coating process is complete.

Coating Conditions for the Application of AQOAT AS-LF Aqueous Coating Dispersion The following coating parameters were used for coating of the AQOAT AS-LF film coating dispersion.

| | |
|---|---|
| Coating Equipment | STREA 1 ™ Table Top Laboratory Fluid Bed Coater |
| Spray nozzle diameter | 1.0 mm |
| Material Charge | 300 gram |
| Inlet Air Temperature | 48° C. |
| Outlet Air Temperature | 27° C. |
| Atomization Air Pressure | 1.6 Bar |
| Pump Rate | 3–4 gram per minute |

Coat Anti-fungal pellets with AQOAT AS-LF film coating dispersion such that you apply 30% coat weight gain to the pellets.

Anti-fungal Pulse Two Pellet Formulation and Preparation Procedure

Preparation of an Eudragit® L 30 D-55 Aqueous Coating Dispersion

Dispersion Formulation

The composition of the aqueous Eudragit L30D-55 aqueous coating dispersion applied to the Anti-fungal pellets is provided below in Table 8.

TABLE 8

Eudragit® L 30 D-55 Aqueous Coating Dispersion

| Component | Percentage (%) |
|---|---|
| Eudragit® L 30D-55 | 44.4 |
| Triethyl Citrate | 1.3 |
| Talc | 6.7 |
| Purified Water* | 47.6 |
| Solid Content | 21.3 |
| Polymer Content | 13.3 |

*Removed during processing

Preparation Procedure for an Eudragit® L 30D-55 Aqueous Dispersion

Disperse triethyl citrate (TEC) in the purified water.
Add the talc into the triethyl citrate dispersion.
Homogenize the dispersion using a homogenizer.
Add the TEC/talc dispersion to Eudragit L30D-55 latex dispersion and stir for at least 30 minutes.
Screen the dispersion through a No. 60 mesh sieve prior to coating.
Continue to stir the dispersion until the coating process is complete.

Coating Conditions for the Application of Eudragit L30D-55 Aqueous Coating Dispersion The following coating parameters were used for coating of the Eudragit® L 30 D-55 film coating dispersion.

| Coating Equipment | STREA 1 ™ Table Top Laboratory Fluid Bed Coater |
|---|---|
| Spray nozzle diameter | 1.0 mm |
| Material Charge | 300 gram |
| Inlet Air Temperature | 45° C. |
| Outlet Air Temperature | 32 to 35° C. |
| Atomization Air Pressure | 1.6 Bar |
| Pump Rate | 3–4 gram per minute |

Coat Anti-fungal pellets with Eudragit L30 D-55 film coating dispersion such that you apply 30% coat weight gain to the pellets.

Anti-fungal Pulse Three Pellets Formulation and Preparation Procedure

Preparation of an AQOAT AS-HF Aqueous Coating Dispersion

Dispersion Formulation

The composition of the aqueous AQOAT AS-HF aqueous coating dispersion applied to the Anti-fungal pellets is provided below in Table 9.

TABLE 9

AQOAT AS-HF Aqueous Coating Dispersion

| Component | Percentage (%) |
|---|---|
| AQOAT AS-HF | 7.0 |
| Triethyl Citrate | 2.0 |
| Talc | 2.1 |
| Sodium lauryl sulfate | 0.2 |
| Purified Water* | 88.7 |
| Solid Content | 11.3 |
| Polymer Content | 7.0 |

*Removed during processing

Preparation Procedure for an AQOAT AS-HF Aqueous Dispersion

Add triethyl citrate (TEC) to the purified water with stirring.
Add the sodium lauryl sulfate (SLS) to the TEC dispersion with stirring and completely until completely dissolved.
Add the AQOAT to the TEC/SLS dispersion and stir for at least 30 minutes.
Add the talc to the AQOAT dispersion and until completely mixed and for at least 30 minutes.
Screen the dispersion through a No. 60 mesh sieve prior to coating.
Continue to stir the dispersion until the coating process is complete.

Coating Conditions for the Application of AQOAT AS-HF Aqueous Coating Dispersion The following coating parameters were used for coating of the AQOAT AS-HF film coating dispersion.

| Coating Equipment | STREA 1 ™ Table Top Laboratory Fluid Bed Coater |
|---|---|
| Spray nozzle diameter | 1.0 mm |
| Material Charge | 300 gram |
| Inlet Air Temperature | 48° C. |
| Outlet Air Temperature | 27° C. |
| Atomization Air Pressure | 1.6 Bar |
| Pump Rate | 3–4 gram per minute |

Coat Anti-fungal pellets with AQOAT AS-HF film coating dispersion such that you apply 30% coat weight gain to the pellets.

Anti-fungal Pulse Four Pellet Formulation and Preparation Procedure

Preparation of an Eudragit® FS 30D Aqueous Coating Dispersion

Dispersion Formulation

The composition of the aqueous Eudragit® FS 30D dispersion applied to the Anti-fungal pellets is provided below in Table 10.

TABLE 10

Eudragit® FS 30D Aqueous Coating Dispersion

| Component | Percentage (%) |
|---|---|
| Eudragit® FS 30D | 54.8 |
| Triethyl Citrate | 0.9 |
| Talc | 3.3 |
| Purified Water* | 41.0 |
| Solid Content | 20.6 |
| Polymer Content | 16.4 |

*Removed during processing

Preparation Procedure for an Eudragit® FS 30D Aqueous Dispersion

Disperse triethyl citrate (TEC) in the purified water.
Add the talc in the triethyl citrate dispersion.
Homogenize the dispersion using a homogenizer.
Add slowly the Eudragit® FS 30D dispersion to the talc/TEC dispersion with stirring.

Continue to stir the coating dispersion until the coating process is complete.

Coating Conditions for the Application of Eudragit FS30D Aqueous Coating Dispersion The following coating parameters were used for coating with each of the Eudragit® FS 30 D aqueous film coating.

| Coating Equipment | STREA 1 ™ Table Top Laboratory Fluid Bed Coater |
|---|---|
| Spray nozzle diameter | 1.2 mm |
| Material Charge | 300 gram |
| Inlet Air Temperature | 38° C. |
| Outlet Air Temperature | 22° C. |
| Atomization Air Pressure | 1.6 Bar |
| Pump Rate | 6 gram per minute |

Coat pellets with Eudragit FS 30D coating dispersion dispersion such that you apply 30% coat weight gain to the pellets.

Anti-fungal Tablets

Tableting of the Anti-fungal Pellets

TABLE 11

Composition of Anti-fungal Tablets

| Component | Percentage (%) |
|---|---|
| Silicified microcrystalline cellulose | 21.5 |
| Lactose monohydrate | 13.0 |
| Povidone | 5.0 |
| Pulse One Pellets | 13.75 |
| Pulse Two Pellets | 13.75 |
| Pulse Three Pellets | 13.75 |
| Pulse Four Pellets | 13.75 |
| Croscarmellose sodium | 5.0 |
| Magnesium stearate | 0.5 |
| Total | 100 |

Blend the silicified microcrystalline cellulose, lactose monohydrate, povidone, colloidal silicon dioxide and Anti-fungal coated pellets for 15 minutes in a tumble blender.

Add the magnesium stearate to the blender, and blend for 5 minutes.

Compress the blend on a rotary tablet press.

The fill weight should be adjusted to achieve the desired dose.

Encapsulation of the Anti-fungal Pellets

Pellets are filled into hard gelatin capsules at a of 25%:25%:25%:25% Pulse One, Pulse Two, Pulse Three and Pulse Four Pellets respectively. The capsule is filled with the four different pellets to achieve the desired dose.

The present invention is particularly advantageous in that there is provided an anti-fungal product which provides an improvement over twice a day administration of the anti-fungal and an improvement over a once a day administration of the anti-fungal.

Numerous modification and variations of the present invention are possible in light of the above teachings and therefore, within the scope of the appended claims the invention may be practiced otherwise than as particularly described.

The present invention is particularly advantageous in that there is provided an anti-fungal product which provides an improvement over twice a day administration of the anti-fungal and an improvement over a once a day administration of the anti-fungal.

Numerous modification and variations of the present invention are possible in light of the above teachings and therefore, within the scope of the appended claims the invention may be practiced otherwise than as particularly described.

What is claimed is:

1. A once-a-day anti-fungal product comprising: first, second, and third anti-fungal dosage forms, each of said anti-fungal dosage forms comprising at least one anti-fungal and a pharmaceutically acceptable carrier, said first, second, and third anti-fungal dosage forms being delayed release dosage forms, and wherein each of said first, second, and third anti-fungal dosage forms initiates release at different times and Cmax of the total anti-fungal released from said anti-fungal product is achieved in less than about 12 hours after initial release of anti-fungal, and said once-a-day anti-fungal product contains the total dosage of the at least one anti-fungal for a twenty-four hour period, said product being free of an immediate release dosage form.

2. The product of claim 1, wherein the Cmax for the product is reached no earlier than four hours after initial release of anti-fungal.

3. The product of claim 1, wherein the anti-fungal released from the first dosage form reaches a Cmax in serum within from about 0.5 hours to about 2 hours after initial release of anti-fungal.

4. The product of claim 1, wherein the anti-fungal released from the second dosage form reaches a Cmax in serum in no more than about 4 hours after initial release of anti-fungal.

5. The product of claim 1, wherein the anti-fungal released from the third dosage form reaches a Cmax in serum within 8 hours after initial release of anti-fungal.

6. The product of claim 1, wherein the first release dosage form contains at least 20% and no more than 50% of the total dosage of anti-fungal.

7. The product of claim 1, wherein the product is an oral dosage form.

8. The product of claim 7, wherein the anti-fungal released from the second dosage form reaches a Cmax in the serum after Cmax is reached in the serum for the anti-fungal released from the first dosage form.

9. The product of claim 8, wherein the anti-fungal released from the third dosage form reaches a Cmax in the serum after Cmax is reached in the serum for the anti-fungal released from the second dosage form.

10. The product of claim 9, wherein said second dosage form initiates release of said anti-fungal before said third dosage form, wherein said second dosage form provides from 30% to 60% by weight of the total anti-fungal released by said second and third dosage forms, and wherein said third dosage form provides the remainder of the total anti-fungal released by said second and third dosage forms.

11. The product of claim 1 further comprising a fourth anti-fungal dosage form, said fourth anti-fungal dosage form comprising at least one anti-fungal and a pharmaceutically acceptable carrier and wherein said at least one anti-fungal released from said fourth anti-fungal dosage form reaches a Cmax in the serum after Cmax is achieved in the serum for anti-fungal released from each of said first, second, and third dosage forms.

12. The product of claim 11, wherein said fourth anti-fungal dosage form is a delayed release dosage form.

13. The product of claim 12, wherein said second dosage form initiates release of said anti-fungal before said third dosage form, wherein said third dosage form initiates release of said anti-fungal before said fourth dosage form, wherein said second dosage form provides 20% to 35% by weight of the total anti-fungal released by said second, third, and fourth dosage forms, wherein said third dosage form provides from 20% to 40% by weight of the total anti-fungal released by said second, third, and fourth dosage forms, and wherein said fourth dosage form provides the remainder of the total anti-fungal released by said second, third, and fourth dosage forms.

14. The product of claim 11, wherein the anti-fungal released from the first dosage form reaches a Cmax in serum within from about 0.5 hours to about 2 hours after initial release of anti-fungal.

15. The product of claim 11, wherein the anti-fungal released from the second dosage form reaches a Cmax in serum in no more than about 4 hours after initial release of anti-fungal.

16. The product of claim 11, wherein the anti-fungal released from the third dosage form reaches a Cmax in serum within 8 hours after initial release of anti-fungal.

17. The product of claim 1, wherein each of said first, second, and third delayed release dosage forms release said at least one anti-fungal agent enterically.

18. The product of claim 17, wherein each of said first, second, and third delayed release dosage forms are pH-sensitive delayed release dosage forms.

19. The product of claim 17, wherein each of said first, second, and third delayed release dosage forms are non-pH-sensitive delayed release dosage forms.

20. The product of claim 17, wherein each of said first, second, and third delayed release dosage forms are each independently selected from the group consisting of pH-sensitive delayed release dosage forms and non-pH-sensitive delayed release dosage forms.

21. A process for treating a fungal infection in a host comprising: administering to a host the anti-fungal product of claim 17 once-a-day.

22. A process for treating a fungal infection in a host comprising: administering to a host the anti-fungal product of claim 18 once-a-day.

23. A process for treating a fungal infection in a host comprising: administering to a host the anti-fungal product of claim 19 once-a-day.

24. A process for treating a fungal infection in a host comprising: administering to a host the anti-fungal product of claim 20 once-a-day.

25. A process for treating a fungal infection in a host comprising: administering to a host the anti-fungal product of claim 1 once-a-day.

26. A process for treating a fungal infection in a host comprising: administering to a host the anti-fungal product of claim 2 once-a-day.

27. A process for treating a fungal infection in a host comprising: administering to a host the anti-fungal product of claim 3 once-a-day.

28. A process for treating a fungal infection in a host comprising: administering to a host the anti-fungal product of claim 4 once-a-day.

29. A process for treating a fungal infection in a host comprising: administering to a host the anti-fungal product of claim 5 once-a-day.

30. A process for treating a fungal infection in a host comprising: administering to a host the anti-fungal product of claim 6 once-a-day.

31. A process for treating a fungal infection in a host comprising: administering to a host the anti-fungal product of claim 7 once-a-day.

32. A process for treating a fungal infection in a host comprising: administering to a host the anti-fungal product of claim 8 once-a-day.

33. A process for treating a fungal infection in a host comprising: administering to a host the anti-fungal product of claim 9 once-a-day.

34. A process for treating a fungal infection in a host comprising: administering to a host the anti-fungal product of claim 10 once-a-day.

35. A process for treating a fungal infection in a host comprising: administering to a host the anti-fungal product of claim 11 once-a-day.

36. A process for treating a fungal infection in a host comprising: administering to a host the anti-fungal product of claim 12 once-a-day.

37. A process for treating a fungal infection in a host comprising: administering to a host the anti-fungal product of claim 13 once-a-day.

38. A process for treating a fungal infection in a host comprising: administering to a host the anti-fungal product of claim 14 once-a-day.

39. A process for treating a fungal infection in a host comprising: administering to a host the anti-fungal product of claim 15 once-a-day.

40. A process for treating a fungal infection in a host comprising: administering to a host the anti-fungal product of claim 16 once-a-day.

41. A once-a-day anti-fungal product for oral administration comprising: first, second, and third anti-fungal dosage forms, each of said anti-fungal dosage forms comprising at least one anti-fungal and a pharmaceutically acceptable carrier, said first, second, and third anti-fungal dosage forms being delayed release dosage forms, and wherein each of said first, second, and third anti-fungal dosage forms initiates release at different times and Cmax of the total anti-fungal released from said anti-fungal product is achieved in less than about 12 hours after initial release of anti-fungal, and said once-a-day anti-fungal product contains the total dosage of the at least one anti-fungal for a twenty-four hour period, said product being free of an immediate release dosage form.

42. A process for treating a fungal infection in a host comprising: administering to a host the anti-fungal product of claim 41 once-a-day.

* * * * *